US00PP36416P2

(12) United States Plant Patent
Carruth

(10) Patent No.: US PP36,416 P2
(45) Date of Patent: Feb. 4, 2025

(54) HYBRID TEA ROSE PLANT NAMED 'WEKmotonton'

(50) Latin Name: *Rosa hybrida*
Varietal Denomination: WEKmotonton

(71) Applicant: Early Morning LLC, Lawrenceburg, IN (US)

(72) Inventor: Thomas F. Carruth, Altadena, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 18/541,817

(22) Filed: Dec. 15, 2023

(51) Int. Cl.
*A01H 5/02* (2018.01)
*A01H 6/74* (2018.01)

(52) U.S. Cl.
USPC ..... Plt./130
CPC ..... *A01H 6/749* (2018.05)

(58) Field of Classification Search
USPC ..... Plt./130
CPC ..... A01H 5/0222
See application file for complete search history.

(56) References Cited

U.S. PATENT DOCUMENTS

PP15,075 P2 8/2004 Zary

OTHER PUBLICATIONS https://www.rose.org/single-post/new-rose-introductions; Oct. 25, 2023; 3 pages.*
https://www.facebook.com/photo.php?fbid=759807939514631&id=100064562954965&set=a.362101779285251&locale=en_GB; Dec. 9, 2023; 1 page.*
https://www.instagram.com/americanrosesociety/p/C0qM6R1KD4a/; Dec. 9, 2023; 1 page.*
https://www.instagram.com/webcoolz/p/CyNFC_AO32b/?locale=pt_PT&img_index=5; Oct. 10, 2023; 2 pages.*
https://www-yuejiw-com.translate.goog/post/22343.html?_x_tr_sl=zh-CN&_x_tr_tl=en&_x_tr_hl=en&_x_tr_pto=sc; Nov. 13, 2023; 1 page.*
Bedard, C., "Grandiflora Rose Plant Named "Weksecjuc"," U.S. Appl. No. 18/390,244, filed Dec. 20, 2023, 10 pages.
Bedard, C., "Shrub Rose Plant Named "Wekblufstow"," U.S. Appl. No. 18/533,666, filed Dec. 8, 2023, 13 pages.
Carruth, T., "Grandiflora Rose Plant Named "Wekalmylcas"," U.S. Appl. No. 18/540,248, filed Dec. 14, 2023, 11 pages.
Make Me Blush TM, "Weeks Roses," 2024 Wholesale Rose Catalog, 2024, 100 pages.

* cited by examiner

*Primary Examiner* — Kent L Bell
(74) *Attorney, Agent, or Firm* — McKee, Voorhees & Sease, PLC

(57) ABSTRACT

A new variety of Hybrid Tea rose suitable for garden decoration, having flowers of soft yellow coloration with pink blush.

1 Drawing Sheet

Classification: The present invention relates to a new *Rosa hybrida* plant.

Variety denomination: The new plant has the varietal denomination 'WEKmotonton'.

BACKGROUND OF THE INVENTION

This invention relates to a new and distinct variety of Hybrid Tea Rose. It has a non-disseminated seedling (unnamed and unpatented) of my creation as its seed parent with the following genetic origin 'Moonstone' x 'Top Notch' (not patented) and as its pollen parent the variety known as 'MACamster' (not patented). It was hybridized by Thomas F. Carruth in 2007 as a result of controlled pollinations performed in a greenhouse in Pomona, California.

SUMMARY OF THE INVENTION

Among the features which distinguish the new variety from other presently available and commercial rose cultivars known to the inventor are the following combinations of characteristics: its elegant high centered soft yellow coloration with pink blush flower, its vigorous growth and its tall growing habit. The plant has an upright somewhat spreading growing habit, suitable for outdoor garden decoration.

Asexual reproduction of the new variety by budding as performed in Kern County, California, shows that the foregoing and other distinguishing characteristics come true to form and are established and transmitted through succeeding asexual propagations. 'WEKmotonton' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, a non-disseminated seedling of my creation by the following combination of characteristics: whereas 'WEKmotonton' bears medium to large sized flowers (about 8.9 to about 12.1 cm. in diameter) of soft yellow coloration with pink blush, the non-disseminated seedling bears significantly smaller flowers (about 6.5 to about 8.3 cm. in diameter) of dark orange with yellow reverse coloration. The new variety has an upright somewhat spreading tall growing habit (about 147 to about 249 cm. in height), whereas the seed parent has an upright moderately spreading significantly shorter growing habit (about 80 to about 110 cm. in height).

The new variety may be distinguished from its pollen parent, 'MACamster' by the following combination of characteristics: whereas 'WEKmotonton' bears medium to large sized flowers (about 8.9 to about 12.1 cm. in diameter) of soft yellow coloration with pink blush, 'MACamster' bears smaller flowers (about 10.8 cm. in diameter) of golden-apricot coloration. The new variety has an upright somewhat spreading tall growing habit (about 147 to about 249 cm. in height), whereas the pollen parent has a bushy upright significantly shorter growing habit (about 90 to about 120 cm. in height).

COMPARISON WITH THE CLOSEST COMMERCIALLY AVAILABLE CULTIVAR

The new variety may be distinguished from its closest commercially available cultivar, 'JACfrepu' (U.S. Plant Pat. No. 15,075) by the following combination of characteristics: whereas 'WEKmotonton' bears medium to large sized flowers (about 8.9 to about 12.1 cm. in diameter) with moderate fruity fragrance, 'JACfrepu' bears larger flowers (about 12.0 cm. to about 13.0 cm. in diameter) with stronger fruity fragrance. The new variety has an upright somewhat spreading tall growing habit (about 147 to about 249 cm. in height), whereas the closest commercially available cultivar has an upright shorter growing habit (about 150 to about 170 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Wasco, California in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Wasco, California in the month of November. Phenotypic expression may vary with environmental, cultural and climatic conditions, as well as differences in conditions of light and soil.

Flower

The new variety usually bears its flowers singly. Flowers are borne on strong somewhat short to long stems (about 23 to about 132 cm.). Outdoors, the plant blooms abundantly and nearly continuously during the growing season. The flowers have a moderate fruity fragrance.

Bud

The peduncle is about 1.6 to about 5.4 cm. in length, of average to somewhat heavy caliper (about 0.2 to about 0.6 cm. in diameter), and usually erect. It is somewhat rough, with few stipitate glands. Peduncle color is between 146D and 146C often heavily suffused, especially on the side exposed to the sun, with between 187B and 187A.

Before the calyx breaks, the bud is about 1.1 to about 1.8 cm. in diameter at the widest point, about 1.6 to about 2.3 cm. in length, and pointed in shape. The surface of the bud bears between 8 to 11 foliaceous appendages with very few stipitate glands and numerous hairs, usually with slender entire foliaceous parts extending beyond the tip of the bud about ½ or more of its length. Bud color is between 138A and 137C often heavily suffused, especially on the side exposed to the sun, with between 187B and 187A.

The sepals are 5 per flower, about 2.1 to about 4.9 cm. in length and about 0.7 to about 1.3 cm. in width at the widest point. The outer surface color of the sepal is between 138A and 137C often heavily suffused, especially on the side exposed to the sun, with between 187B and 187A. The outer surface of the sepal is smooth and bears between 0 to 5 foliaceous appendages with very few stipitate glands and numerous hairs. The inner surface color of the sepal is near 146D broadly bordered by near 137B. After the sepals open, the inner surface color is often heavily suffused, especially on the area exposed to the sun, with between 187B and 187A. The inner surface of the sepal is covered with fine wooly tomentum; sepal margins are entire and lined with few stipitate glands and numerous hairs. The sepals are moderately permanent, and usually straight in shape with acute apices.

The receptacle of the flower is of medium to somewhat long length (about 0.5 to about 1.2 cm.) and somewhat thin to average in caliper (about 0.3 to about 1.1 cm. in diameter). The receptacle is urn-shaped in form. Its surface is smooth with moderately thick fleshy walls. The receptacle color is between 144A and 146C sometimes heavily suffused, especially on the side exposed to the sun, with between 187B and 187A.

As the petals open (after the calyx breaks), the bud is about 1.9 to about 2.5 cm. in diameter at the widest point, about 2.6 to about 4.0 cm. in length, and pointed to somewhat ovoid in form. The color of the under surfaces of the newly opened petals is between 1A and 2C often heavily suffused with between 60A and 60B to as dark as between 187B and 187C. There is no visible change in coloration at the point where the petal attaches. The color of the upper surfaces of the newly opened petals is between 1B and 1A. There is no visible change in coloration at the point where the petal attaches.

Bloom

When fully open, the bloom ranges from about 8.9 to about 12.1 cm. in diameter. Petalage is double with about 23 to 46 petals and about 2 to 10 petaloids irregularly arranged. When partially open, the bloom form is ovoid to moderately high centered to cupped, and the petals are moderately tightly spiraled to cupped with petal edges somewhat reflexed outward. When fully open, the bloom form is more cupped, and the petals are loosely cupped to somewhat undulated with petal edges somewhat reflexed outward.

Petals

The substance of the petals is moderately heavy and of somewhat thin to medium thickness, with upper surfaces slightly shiny and under surfaces moderately shiny. The petals are about 4.5 to about 7.0 cm. in length and about 2.7 to about 7.2 cm. in width at the widest point. Petal margins are entire.

The outer petals are nearly rounded in shape with rounded apices.

The inner petals are moderately obovate to somewhat oblanceolate in shape with rounded apices.

Petaloids are about 0.8 to about 4.8 cm. in length and about 0.3 to about 2.8 cm. in width at the widest point. Petaloids are irregularly shaped moderately oblanceolate to somewhat obovate to subulate with rounded apices.

Newly Opened Flower

The under-surface color of the outer petals is between 4C and 11B often moderately suffused on the outermost petals with between 60D and 59D to as dark as between 60A and 60B. There is no visible change in coloration at the point where the petal attaches. The upper surface color of the outer petals is between 10C and 11A often lightly suffused with between 60D and 59D. At the point where the petal attaches, there is a small zone of between 9A and 9B.

The under-surface color of the intermediate and inner petals is between 4C and 11B. The upper surface color of the intermediate and inner petals is between 10C and 11A.

The under and upper surface colors of the petaloids are similar in coloration to the upper and under surfaces of the intermediate and inner petals.

The general tonality of the newly opened flower is between 10C and 11A.

Three-Day-Old Flower

The under-surface color of the outer petals is lighter than 2D and between 155B and 155D often heavily suffused with between 60D and 59D to as dark as between 60A and 60B. There is no visible change in coloration at the point where the petal attaches. The upper surface color of the outer petals is lighter than 2D and between 155D and 155B often moderately suffused with between 60D and 59D to as dark as between 60A and 60B. At the point where the petal attaches, there is a moderately small zone of between 11A and 10A.

The under-surface color of the intermediate and inner petals is between 2D and 11B sometimes lightly suffused with between 60D and 59D. The upper surface color of the intermediate and inner petals is between 2D and 11B sometimes lightly suffused with between 60D and 59D.

The under and upper surface colors of the petaloids are similar in coloration to the upper and under surfaces of the intermediate and inner petals.

The general tonality of the three-day-old flower is between 2D and 11B sometimes lightly suffused with between 60D and 59D.

On the spent bloom, the petals usually drop off, fading to between 155D and 155B.

In November in Wasco, California, blooms on the bush growing outdoors generally last about four to five days. Cut roses from plants grown outdoors and kept at normal indoor living temperatures generally last about four to five days.

Male Reproductive Organs

Stamens are many in number (average about 195) and are arranged regularly about the pistils; a few are mixed with petaloids. The filaments are of somewhat short to medium length (about 0.4 to about 1.0 cm.) most with anthers. Filaments are between 5A and 6B in color. The anthers are of medium to somewhat large size for their class and all open approximately at the same time. Anther color when immature is near 21C on the external part and near 8D on the internal part. Anther color at maturity is near 164D on the external part and near 200A on the internal part. Pollen is abundant and between 11C and 12D in color.

Female Reproductive Organs

Pistils vary in number (average about 110). The styles are uneven, short to long in length (about 0.3 to about 0.9 cm.), thin in caliper, and loosely bunched. Stigma color is between 1B and 1A. Style color is between 4D and 2D. Ovaries are usually all enclosed in the calyx. The ovaries are of medium size and between 158A and 161D in color.

Hips have not been observed on this variety when grown in Wasco, California.

Foliage

The compound leaves are usually comprised of three to seven leaflets and are borne abundantly. The five-leaflet leaves are about 9.2 to about 17.5 cm. in length and about 6.5 to about 15.8 cm. in width at the widest point, leathery to moderately crisp in texture on both sides, and glossy in finish on the upper side and semi-glossy in finish on the underside. The leaves have a pinnate venation pattern. The terminal leaflets are about 4.6 to about 8.8 cm. in length and about 2.9 to about 5.5 cm. in width at the widest point, shaped ovate to somewhat oval with acute apices and rounded bases. Their margins are usually simply serrate.

The upper surface color of the mature leaf is between 137A and 139A. The under-surface color of the mature leaf is between 146B and 148B. The under and upper colors of the leaf veins on the mature leaf are similar in coloration to the upper and under surfaces colors of the mature leaf. The upper surface color of the young leaf is between 137A and 147A, usually heavily suffused with between 187A and 187B. The under-surface color of the young leaf is between 146B and 148B, usually heavily suffused with between 187B and 187A. The under and upper colors of the leaf veins on the young leaf are similar in coloration to the upper and under surfaces colors of the young leaf.

The rachis is about 2.2 to about 5.0 cm. in length, about 0.1 to about 0.2 cm in width at the widest point, and rough. The upper side is deeply grooved with very few hairs and few stipitate glands on the edges of the grooves. The under side of the rachis is rough with few stipitate glands and small prickles. The rachis color is near 145B on the underside and near 146B on the upper side, often heavily suffused on the young leaves with between 187B and 187A.

The stipules are about 1.5 to about 2.6 cm. in length and of medium width to somewhat wide (about 0.4 to about 1.1 cm.) with moderately long straight points that usually turn out at an angle of more than 45 degrees and often recurve toward the stem. The under and upper surface color of the stipule is between 137B and 137C. The upper and under surfaces of the stipules are smooth in texture.

The petiole is somewhat light to average in caliper and rough. The upper side is deeply grooved with very few hairs and few stipitate glands on the edges of the grooves. The under side of the petiole is rough with few stipitate glands and small prickles. The petiole is about 0.3 to about 2.1 cm. in length and about 0.1 to about 0.2 cm in width at the widest point. The petiole color is near 145B on the underside and near 146B on the upper side, often heavily suffused on the young leaves with between 187B and 187A.

The plant displays an above average degree of resistance to powdery mildew (*Sphaerotheca pannosa*), downy mildew (*Peronospora sparsa*) and rust (*Phragmidium* sp.) as compared to other commercial varieties grown under comparable conditions in Wasco, California. The plant's winter hardiness and drought/heat tolerance are yet to be determined.

Growth

The plant has an upright somewhat spreading tall growing habit (about 147 to about 249 cm. in height and about 91 to about 122 cm. spread at the widest point), with full branching. It displays vigorous growth and the canes are of somewhat light to medium caliper for the class (about 1.0 to about 2.1 cm. in diameter at the widest point).

The color of the major stems is between 148A and 152B. The major stems are rough in texture and they bear many large prickles that are about 0.5 to about 1.0 cm. in length. The large prickles are angled moderately downward with a medium length somewhat broad oval base; prickle color is between 164B and 165C usually heavily suffused with between 201B and 201C. The major stem bears few small prickles of similar shape and coloration.

The color of the branches is between 146C and 147B. The branches are rough in texture and they bear many large prickles which are of similar size and shape to the large prickles on the major stems; prickle color is between 160A and lighter than 152D sometimes moderately suffused with between 187C and 187D. The branches bear few small prickles of similar shape and coloration.

The color of the new shoots is between 146B and 147B often moderately suffused with between 187B and 187A. The new shoots are rough in texture and they bear many large prickles which are of similar size and shape to the large prickles on the major stems; prickle color is between 160A and lighter than 152D sometimes moderately suffused with between 187B and 187C. The shoots bear few small prickles of similar shape and coloration.

I claim:

1. A new and distinct Hybrid Tea rose plant of the variety designated 'WEKmotonton' substantially as described and illustrated herein.

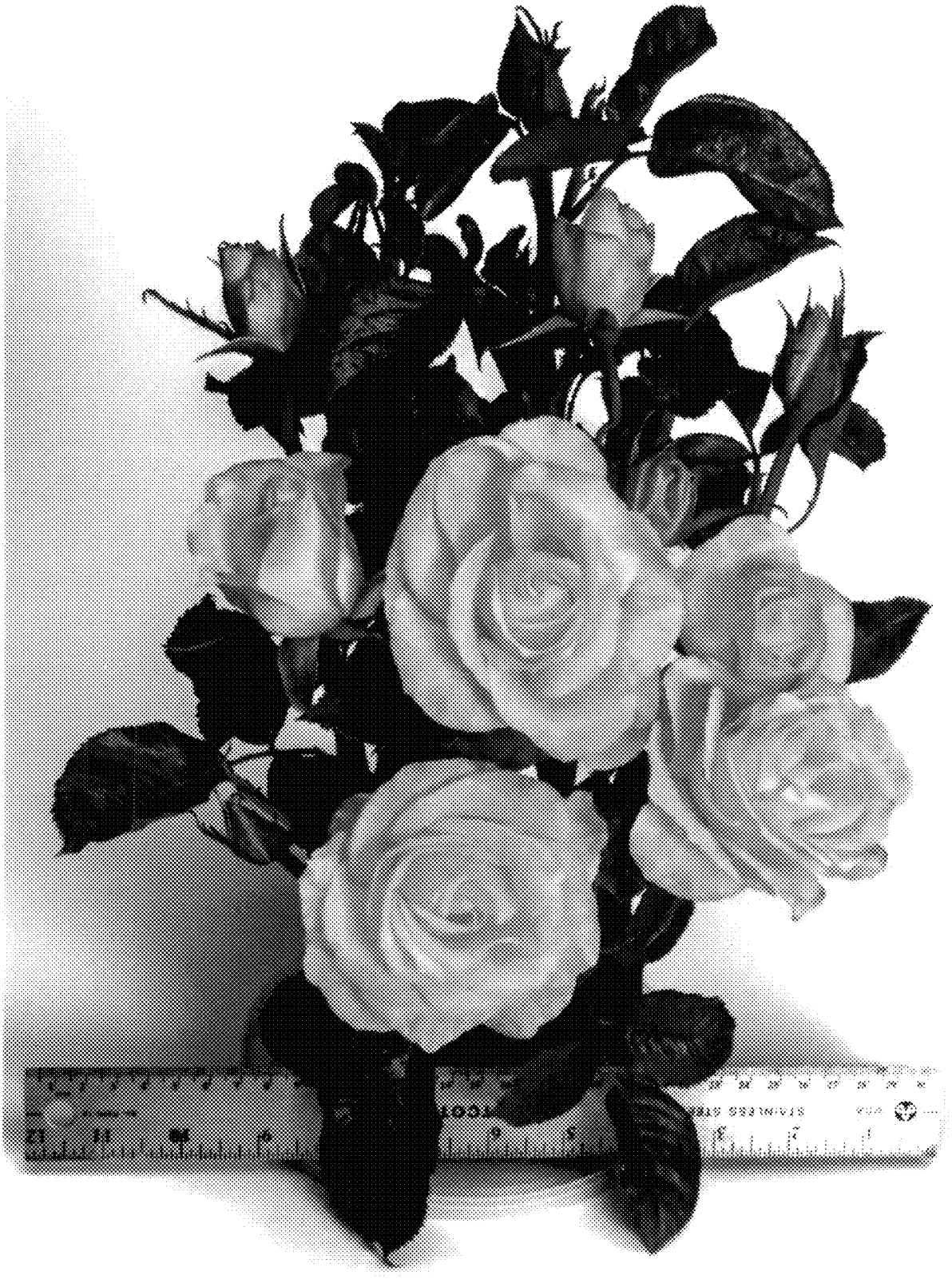

* * * * *